United States Patent [19]

Venero et al.

[11] Patent Number: 4,894,449

[45] Date of Patent: Jan. 16, 1990

[54] DIOSMIN OCTAKIS (HYDROGEN SULFATE) ALUMINUM COMPLEX

[76] Inventors: Aurelio O. Venero, Paseo del Puerto, 24 48990 Neguri; Ramon M. Pestana, Avenida Iparraguirre, 20, 7° A, 48940 Lejona, both of Spain

[21] Appl. No.: 225,544

[22] Filed: Jul. 28, 1988

[30] Foreign Application Priority Data

Jul. 7, 1987 [EP] European Pat. Off. ...... 87.500.053.1
Jul. 7, 1987 [ES] Spain .................................... 8702270

[51] Int. Cl.$^4$ .................... C07H 11/00; C07H 15/00; C07H 17/06; C07H 15/24
[52] U.S. Cl. .................................. 536/118; 536/17.1; 536/8; 536/8.8; 536/18.1
[58] Field of Search ..................... 536/118, 17.1, 18.1, 536/8.8, 8

[56] References Cited

U.S. PATENT DOCUMENTS

| | | | |
|---|---|---|---|
| 3,432,489 | 3/1969 | Nitta et al. | 536/118 |
| 4,334,058 | 6/1982 | Nair et al. | 536/8 |
| 4,342,753 | 8/1982 | Nair et al. | 536/118 |

Primary Examiner—Ronald W. Griffin
Assistant Examiner—Everett White
Attorney, Agent, or Firm—Davis Hoxie Faithfull & Hapgood

[57] ABSTRACT

The invention refers to the preparation of diosmin octakis (hydrogen sulfate) aluminum complex, a new derivative of diosmin, by reaction of diosmin with a sulfating agent, such as sulfur trioxide-pyridine complex, sulfur trioxide-trimethylamine complex and sulfur trioxide-triethylamine complex, at a temperature between 40° and 110° C., in an appropriate medium, with preference pyridine, dimethylformamide and dimethylacetamide, and final addition of aluminum hydroxychloride.

1 Claim, No Drawings

DIOSMIN OCTAKIS (HYDROGEN SULFATE) ALUMINUM COMPLEX

Diosmine is a polyhydroxylated flavone with eight hydroxyl groups, two of them are phenolic and the other six being in the sugar rest, and is able to undergo different reactions being esterification one of them.

Diosmine can give esters when it is treated with a reactive derivative of organic and inorganic acids in a suitable solvent. In particular Diosmine forms esters from sulfuric acid when it reacts with a sulfating agent, varying the esterification index with the conditions of the reactions, especially with the molar ratio of diosmine/sulfating agent. In certain conditions it is possible to esterify all the hydroxyl groups of the molecule and to afford the octasulfate of diosmine.

The sulfur trioxide-pyridine complex or the sulfur trioxide-trialkylamine complexes are used as sulfating agents. The first of these is obtained from chlorosulfonic acid or from the sulfur trioxide and the pyridine, and it can be prepared and purified previous to its use of formed in situ in the reaction vessel. The sulfur trioxide-pyridine complex sulfates substances such as hydrazine, dyethylamine, phenol and naphthalene, and it has been used in preparation of carbohydrate, sterol and phenol sulfate esters. The sulfur trioxide-trialkylamine complexes, especially those formed with trimethylamine and triethylamine, are also useful to carry out the reaction. They are mild agents, sulfating alcohols or phenols.

In the present invention, the preparation of a new diosmine derivative is described. The diosmine derivative is an diosmin octakis (hydrogen sulfate) aluminium complex which has a great pharmacological interest.

The product administered orally in doses of 200 mg/kg to rats with gastric lesions induced by pure ethanol (following the technique of A. Robert et al., Gastroenterology, 77, 433–443 (1979)) significantly protected the gastric mucosa.

In another experiment carried out in accordance with Shay et al's method (Gastroenterology, 5, 43–61 (1945)) the diosmin octakis (hydrogen sulfate) aluminium complex significantly protected the glandular and aglandular region of the stomach at doses of 100 and 200 mg/kg., when it was administered orally immediately after the pilorus ligation.

Besides the gastric mucosa protective activity and acid-consuming capacity of the diosmin octakis (hydrogen sulfate) and aluminium complex, it lacks of undesirable side effects.

The preparation of the diosmin octakis (hydrogen sulfate) aluminium complex is carried out by the reaction of the diosmine with the sulfur trioxide-pyridine complex or with the sulfur trioxide-trialkylamine complexes, using the sulfating agents in an excess.

The solvent employed in the sulfation of Diosmine is chosen among pyridine, dimethylformamide and dimethylacetamide and the temperature at which the reaction takes places can osilate between 40° and 110° C. without a substantial variation in the result of the process, but logically at low temperatures the completion of the reaction takes more time.

The aluminium salt of the diosmine octasulfate can be made from the corresponding sodium salt or from the corresponding ammonium salt by adding aluminium hydroxychloride in an aqueous solution.

The following examples of the preparation of the diosmin octakis (hydrogen sulfate) aluminium complex illustrate the invention but are not exhaustive.

EXAMPLE 1

A mixture of 10 g. of diosmine and 25 g. of the sulfur trioxide-pyridine complex in 100 ml. of pyridine is heated at a temperature of 60° C. for 5 hours with stirring. The upper layer of pyridine is separated by decantation and the lower one is neutralized with concentrated aqueous sodium hydroxide. Ethyl alcohol is added dropwise until a precipitate begins to form. This deposit is filtered off and more ethyl alcohol is added to the liquid part. The new solid formed is separated by filtration and is washed several times with ethyl alcohol. It is dried at room temperature in vacuum (16,7 g.). It is dissolved in 200 ml. of distilled water and 130 ml. of a 15% solution of aluminium hydroxychloride is added. The resulting yellow solid is filtered, washed several times with water and is dried in vacuum at room temperature (26 g.). M.P. higher than 250° C.

IR (3490, 1640 cm$^{-1}$).

$C_{28}H_{64}Al_{16}O_{79}S_8$, calculated: Al 18,34: S 10,90. Found: Al 18,71; S 10,81.

EXAMPLE 2

10 g. of diosmine and 24 g. of the sulfur trioxide-trimethylamine complex is heated in 40 ml. of dimethylformamide for 2 hours at a temperature of 90° C. The mixture is cooled at room temperature and then poured into 400 ml. of acetone with stirring. The upper layer is separated by decantation and the lower layer is washed twice with acetone. It is the dissolved in water and 150 ml. of a 15% solution of aluminium hydroxychloride is added. The solid which forms is filtered, washed in water and dried. 17 g. of the product described in Example 1. are obtained.

What is claimed is:

1. Diosmin octakis (hydrogen sulfate) aluminium complex, with molecular formula:

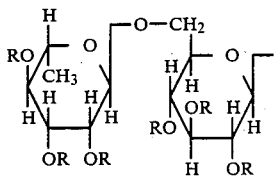

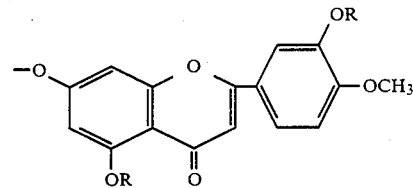

in which R represents $SO_3Al_2(OH)_5$.

* * * * *

UNITED STATES PATENT AND TRADEMARK OFFICE
CERTIFICATE OF CORRECTION

PATENT NO. : 4,894,449

DATED : January 16, 1990

INVENTOR(S) : Venero et al.

It is certified that error appears in the above—identified patent and that said Letters Patent is hereby corrected as shown below:

Column 1, line 22, change "of" to --or--;

Column 1, line 60, change "places" to --place--;

Column 2, line 36, change "the" to --then--.

Signed and Sealed this

Eleventh Day of December, 1990

Attest:

HARRY F. MANBECK, JR.

*Attesting Officer*   *Commissioner of Patents and Trademarks*